(12) United States Patent
Allan et al.

(10) Patent No.: US 6,541,666 B2
(45) Date of Patent: Apr. 1, 2003

(54) PROCESS FOR THE CO-PRODUCTION OF ACETIC ANHYDRIDE AND ACETIC ACID

(75) Inventors: Robert Edward Allan, East Yorkshire (GB); Derrick John Watson, East Yorkshire (GB)

(73) Assignee: BP Chemicals Limited, London (GB)

( * ) Notice: Subject to any disclaimer, the term of this patent is extended or adjusted under 35 U.S.C. 154(b) by 200 days.

(21) Appl. No.: 09/746,067

(22) Filed: Dec. 26, 2000

(65) Prior Publication Data

US 2001/0007912 A1 Jul. 12, 2001

(30) Foreign Application Priority Data

Dec. 23, 1999 (GB) .............................................. 9930599

(51) Int. Cl.$^7$ .............................................. C07C 51/54
(52) U.S. Cl. ....................................................... 562/890
(58) Field of Search ......................................... 562/890

(56) References Cited

U.S. PATENT DOCUMENTS

| 4,374,070 A | 2/1983 | Larkins et al. |
| 5,214,205 A | 5/1993 | Castanet et al. |

FOREIGN PATENT DOCUMENTS

| EP | 0 060 695 A1 | 9/1982 |
| EP | 0 087 870 A1 | 9/1983 |
| EP | 0 109 212 B1 | 5/1984 |
| EP | 0 135 286 A1 | 3/1985 |
| EP | 0 144 949 A2 | 6/1985 |
| EP | 0 146 823 A1 | 7/1985 |
| JP | 62-145041 | 6/1987 |

OTHER PUBLICATIONS

Bryant et al, "The Rhodium Catalyzed . . . General Papers—Petrochemicals . . . " American Chemical Society, Dallas Meeting, Apr. 8–13, 1973.
Cheong et al, "Nickel—catalysed Isomerization . . . ," Journal of the Chemical Society, Chemical Comm., No. 9, pp. 661–666 (1990).
Bub et al, "On the rhodium catalyzed . . . ," Journal of Molecular Catalysis A: Chemical 95, pp. 45–52 (1995).
Schreck et al, "A highly effective catalyst . . . " Journal of Molecular Catalysis, vol. 47, pp. 117–121 (1988).
Pruett et al, "Reactions of Formic Acid . . . " Organometallics, vol. 1, pp. 1693–1699 (1982).
American Chemical Society, 118:59298 "Preparation of acetic anhydride from methyl formate" (1997).
American Chemical Society, 118:149793 "Synthesis of acetic acid by isomerization . . . " (1997).
American Chemical Society, 123:260317 "An effective rhodium catalyst system on teh synthesis of acetic acid from methyl" (1997).
American Chemical Society, 126:330338 "Rhodium–iodide catalyzed carbonylation of methyl formate . . . " (1998).
American Chemical Society, Carbonylation catalyst . . . (1998).
American Chemical Society, 129:277672 "Continuous manufacture of acetic acid from methyl . . . " (1999).
American Chemical Society, 109:44290 "Rhodium catalyzed reductive carbonylation . . . " (1997).
American Chemical Society, 113:190684 "Selective methyl formate homologation into methyl . . . " (1997).
American Chemical Society, 115:231624 "Isomerization and carbonylaton of esters catalyzed . . . " (1997).
American Chemical Society, 113:23070 "Isomerization of methyl formate and carbonylation . . . " (1997).
American Chemical Society, 108:94069 "Simultaneous synthesis of acetic acid and . . . " (1997).

*Primary Examiner*—Paul J. Killos
(74) *Attorney, Agent, or Firm*—Nixon & Vanderhye

(57) ABSTRACT

A process for the co-production of acetic anhydride and acetic acid which process comprises introducing a carbonylatable feedstock comprising methyl acetate and/or dimethyl ether and optionally also comprising methanol and/or water, to a carbonylation reactor in which there is maintained a liquid reaction composition comprising acetic anhydride, acetic acid, rhodium carbonylation catalyst, alkyl iodide co-catalyst and an iodide salt promoter consisting essentially of an alkali metal iodide and/or alkaline earth metal iodide, contacting said carbonylatable feedstock with carbon monoxide in said liquid reaction composition to produce acetic anhydride and acetic acid, and introducing to the carbonylation reactor methyl formate and/or formic acid in the range from 0.1 to 20% by weight of the total feed of liquid components to the reactor.

10 Claims, 1 Drawing Sheet

Figure 1:
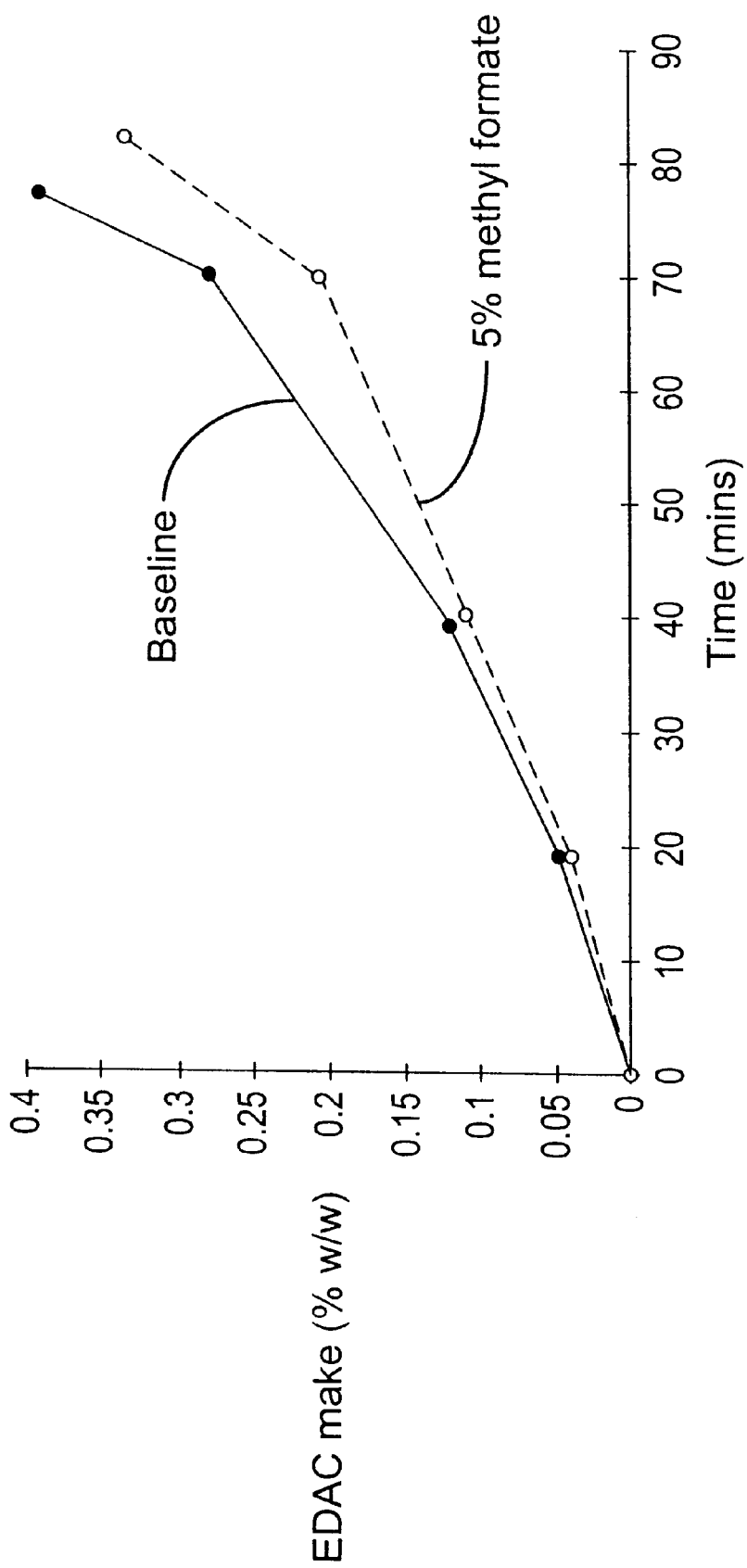

Graph of EDAC make vs Batch reaction run time.

PROCESS FOR THE CO-PRODUCTION OF ACETIC ANHYDRIDE AND ACETIC ACID

The present invention relates to a process for the co-production of acetic anhydride and acetic acid and in particular to a process for the co-production of acetic anhydride and acetic acid by carbonylation of a carbonylatable feedstock comprising methyl acetate and/or dimethyl ether and optionally also comprising methanol and/or water, in the presence of a rhodium carbonylation catalyst, alkyl iodide co-catalyst and an iodide salt promoter.

Processes for the production of acetic anhydride by carbonylation in the presence of a rhodium carbonylation catalyst, alkyl iodide co-catalyst and lithium iodide promoter are known, for example from U.S. Pat. No. 4,374,070 which relates to the production of acetic anhydride in the presence of rhodium, an iodine compound and lithium.

The carbonylation of a feedstock comprising methanol, methyl acetate and water to produce a mixture of acetic acid and acetic anhydride is described in EP-A-087870.

Preparation of acetic acid by isomerisation of methyl formate under substantially anhydrous conditions in the presence of carbon monoxide and a rhodium catalyst, halide promoter and quaternary Group V atom is described in EP-B-0109212.

EP-A-0144949 describes a process for the production of organic carboxylic acids from formic acid and organic esters in contact with a catalyst system consisting essentially of rhodium metal atom and lithium iodide. In the examples relatively large amounts of formic acid are used and acetic anhydride is not produced.

Seuillet et al in Applied Catalysis A 93 (1993) 219–229 describe acetic anhydride synthesis from methyl formate catalysed by rhodium-iodide complexes. According to Seuillet et al, the synthesis proceeds via the homologation of methyl formate into methyl acetate followed by carbonylation of the latter. According to Seuillet et al the influence of various parameters on the two steps is different such that the "one pot" synthesis of acetic anhydride from methyl formate requires a two steps procedure. Such a two step procedure is described in U.S. Pat. No. 5,214,205. According to Seuillet et al when methyl formate is added to conditions optimised for production of acetic anhydride from methyl acetate (methyl formate/methyl acetate=0.1), the initial reaction consists of the production of acetic acid and methyl acetate (via a transesterification process), with the anhydride appearing only when methyl formate has almost disappeared. According to Seuillet et al during these runs, methyl formate and acetic anhydride were never observed simultaneously. Seuillet et al performed their experiments in a batch autoclave.

Japanese laid-open patent application S62[1987]-145041 describes the simultaneous manufacture of acetic acid and acetic anhydride by heating methyl formate and methyl acetate under pressure of carbon monoxide in the presence of a rhodium catalyst, iodine compounds and accelerating agents comprising aluminium and boron compounds.

There remains a need for an improved process for the co-production of acetic anhydride and acetic acid.

It has now been found that if methyl formate and/or formic acid is/are introduced into a process for the co-production of acetic anhydride and acetic acid by carbonylation of a carbonylatable feedstock comprising methyl acetate and/or dimethyl ether and optionally also comprising methanol and/or water, in the presence of a rhodium carbonylation catalyst, alkyl iodide co-catalyst and an iodide salt promoter consisting essentially of an alkali metal iodide and/or alkaline earth metal iodide, not only is acetic anhydride produced at acceptable rates, but the amounts of by-products such as ethylidene diacetate are reduced.

This finding is unexpected particularly in view of the teaching of Seuillet et al that the conditions favourable to the production of acetic anhydride from methyl acetate are unfavourable to the formation of methyl acetate from methyl formate.

Thus according to the present invention there is provided a process for the co-production of acetic anhydride and acetic acid which process comprises introducing a carbonylatable feedstock comprising methyl acetate and/or dimethyl ether and optionally also comprising methanol and/or water, to a carbonylation reactor in which there is maintained a liquid reaction composition comprising acetic anhydride, acetic acid, rhodium carbonylation catalyst, alkyl iodide co-catalyst and an iodide salt promoter consisting essentially of an alkali metal iodide and/or alkaline earth metal iodide, contacting said carbonylatable feedstock with carbon monoxide in said liquid reaction composition to produce acetic anhydride and acetic acid, and introducing to the carbonylation reactor methyl formate and/or formic acid.

In the process of the present invention, the methyl formate and/or formic acid is a valuable source of the components of carbon monoxide and can be used to advantage in a location where a source of these compounds is available adjacent to an existing carbonylation process for the production of acetic anhydride. Furthermore, not only has it been found that the introduction of methyl formate and/or formic acid does not have an adverse effect on the carbonylation rate, but also the presence of these compounds reduces the formation of by-products when the carbonylation process uses an iodide salt promoter consisting essentially of an alkali metal iodide and/or alkaline earth metal iodide.

In the process of the present invention the carbonylatable feedstock comprises methyl acetate and/or dimethyl ether and optionally, also comprises methanol and/or water. Acetic anhydride is produced by the carbonylation of methyl acetate and/or dimethyl ether. Acetic acid is produced from methanol, water, methyl formate and/or formic acid. Thus the proportions of acetic anhydride and acetic acid produced are dependent upon the relative amounts of these components of the feedstock. It is important that the amount of methanol, water, methyl formate and/or formic acid should not be so large that the amount of acetic anhydride produced is insufficient to maintain a concentration of acetic anhydride in the liquid reaction composition. Suitable carbonylatable feedstocks include methyl acetate/methanol mixtures, dimethyl ether/methanol mixtures and methyl acetate/methanol/water mixtures.

The amount of methyl formate and/or formic acid introduced into the carbonylation reactor is suitably in the range from 0.1 to 20% by weight of the total feed of liquid components to the reactor, preferably in the range from 0.1 to 10% by weight of the total feed of liquid components to the reactor, provided that the amount of methanol, water, methyl formate and/or formic acid is not so great that there is no acetic anhydride maintained in the liquid reaction composition in the reactor.

It has been found that methyl formate will be present in the liquid reaction composition, suitably at a concentration in the range from greater than zero to 1000 ppm. However, when formic acid is introduced into the reactor rather than methyl formate, this decomposes more quickly than methyl formate and it has been found that there is a lower standing concentration of formic acid in the liquid reaction composition, suitably in the range from greater than zero to 100 ppm.

The process of the present invention is suitable performed at a temperature in the range from 150 to 220° C., preferably in the range from 175 to 200° C.

The process of the present invention is suitably performed at a pressure in the range from 1000 kPa to 10000 kPa, preferably at a pressure in the range from 2000 to 5000 kPa.

Carbon monoxide used in the present invention is preferably at least 95% pure. Suitable impurities are hydrogen, carbon dioxide, methane, nitrogen, noble gases and $C_1$ to $C_4$ hydrocarbons. Preferably, the amount of hydrogen in the carbon monoxide used is in the range from 0 to 10.0% by volume.

The rhodium carbonylation catalyst may be pre-formed and added to the liquid reaction composition or may be formed in situ in the liquid reaction composition. Suitable rhodium compounds which may be used for the formation of the rhodium carbonylation catalyst include $[Rh(CO)_2Cl]_2$, $[Rh(CO)_2I]_2$, $[Rh(Cod)Cl]_2$, rhodium (III) chloride, rhodium (III) chloride trihydrate, rhodium (III) bromide, rhodium (III) iodide, rhodium (III) acetate, rhodium dicarbonylacetylacetonate, $RhCl_3(PPh_3)_3$ and $RhCl(CO)(PPh_3)_2$. The concentration of the rhodium carbonylation catalyst in the liquid reaction composition is suitably in the range from 50 to 2000 ppm rhodium, preferably in the range from 100 to 1000 ppm rhodium.

Preferably, the alkyl iodide is methyl iodide. The concentration of alkyl iodide in the liquid reaction composition is suitably in the range from 1 to 30% by weight, preferably in the range from 5 to 20% by weight.

More than one alkali metal iodide salt and/or alkaline earth metal iodide salt may be used in the process of the present invention. For the avoidance of doubt, the alkali metals are lithium, sodium, potassium, rubidium, cesium and francium and the alkaline earth metals are beryllium, magnesium, calcium, strontium, barium and radium. Preferably, the iodide salt promoter consists essentially of lithium iodide. It has been found that the use of iodide salts other than alkali metal iodides or alkaline earth metal iodides does not show benefits when methyl formate and/or formic acid is introduced to the carbonylation process. The concentration of iodide salt promoter in the liquid reaction composition is suitably in the range from 1 to 40% by weight.

Methyl acetate, acetic acid and acetic anhydride will be present in the liquid reaction composition maintained in the reactor. Suitably, the concentration of methyl acetate in the liquid reaction composition will be maintained in the range from 1 to 30% by weight, preferably in the range from 5 to 30% by weight. Suitably, the concentration of acetic acid in the liquid reaction composition will be maintained in the range from 0.1 to 50% by weight. Suitably, the concentration of acetic anhydride in the liquid reaction composition will be maintained in the range from 0.1 to 30% by weight.

The acetic acid and acetic anhydride product may be recovered from the carbonylation reactor, by continuously removing a portion of the liquid reaction composition from the carbonylation reactor, recovering the acetic acid and acetic anhydride products therefore and recycling the remaining components to the carbonation reactor. This may be performed by processes know in the art. Thus, for example, the withdrawn liquid reaction composition may be passed with or without the addition of heat to a flash separation zone from which a vapour fraction containing the acetic acid and acetic anhydride product is separated from a liquid fraction comprising rhodium carbonylation catalyst and alkali/alkaline earth metal iodide salt The acetic acid and acetic anhydride are recovered from the vapour fraction in one or more distillative separation stages, with the other components such as methyl acetate, alkyl iodide and acetic acid being recycled to the carbonylation reactor. The liquid fraction from the flash separation stage is recycled to the carbonylation reactor. A suitable carbonylation process and separation process are described by Howard et al in *Catalysis Today*, 18 (1993) 325–354 at section 3.2 pages 334–339, the contents of which are incorporated by reference.

The invention will now be described by reference to the following examples and FIG. 1 which is a graph of the formation of ethylidene diacetate by-product in batch carbonylation experiments with and without methyl formate addition. In the experiments the abbreviation EDAc means ethylidene diacetate.

Batch Autoclave Experiments

General Experimental Procedure

These experiments were performed using a Parr 300 ml autoclave, constructed from Hastelloy HB2 (Trade Mark). This was provided with a gas dispersion impeller system which was operated at 1500 rpm. Prior to each carbonylation reaction, the autoclave was pressure tested with nitrogen at or above the intended reaction pressure. This was usually carried out with the promoter and 10–15 g acetic acid already charged to the autoclave. Once it had been confirmed that the autoclave was pressure tight, the autoclave was vented.

Most reactions involved an initial charge of hydrogen to the autoclave. Therefore, the gas supply lines and manifold were flushed with hydrogen 3 times. The autoclave was then flushed three times with hydrogen at a pressure of 500 kPaG (5 barg) and vented. The liquid reagents were charged to the autoclave (through a funnel or liquid charging bomb). The autoclave was then charged with the required initial pressure of hydrogen. The gas supply lines and manifold were then flushed with the feed gas for the reaction (usually pure CO) and the autoclave was charged up to one-third the reaction pressure and then heated up to 185° C. When stable at temperature (10–15 minutes) the pressure was topped up to 400 kPaG (4 barg) below the reaction pressure and the catalyst (in 15 g solution) injected using an 1100 kPaG (11 barg) over pressure of the feed gas. The reaction was then maintained at the reaction pressure (±50 kPaG (0 5 barg)) using a control valve/ballast vessel. Excess heat of reaction was removed by an automatically controlled cooling finger, the coolant being water (DT=±5° C.) The reaction was terminated once gas uptake had ceased or after a fixed time. The heater was turned off and the cooling water set to maximum. Once the autoclave was cool (<40° C.) the pressure and temperature were recorded prior to gas sampling. The gas sample bomb was flushed twice with the reactor gas up to a pressure of 400 kPaG (4 barg) before filling with gas from the reactor up to a pressure of 800–900 kPaG (8–9 barg) for analysis.

Analysis of the liquid by-products was carried out using a dedicated gas chromatograph. Gas analysis was carried out on an ATI Unicam 610 series gas chromatogram.

The rate of reaction was determined by measuring the fall in pressure of carbon monoxide in a supply ballast vessel. From this was calculated the rate in units of mol/l/hr.

Four experiments were performed without methyl formate addition. In Experiments A and B, the amount of reagents charged were adjusted by increasing the amounts of methyl acetate and acetic acid and reducing the amount of acetic anhydride, so that they corresponded to that which would have resulted had methyl formate been present and had converted some of the acetic anhydride to acetic acid according to the equation 1 gmol methyl formate+1 gmol acetic anhydride=1 gmol. methyl acetate+1 gmol. acetic acid+1 gmol carbon monoxide. In Experiments C and D, methanol was added equivalent on a molar basis to 5% by weight methyl formate to convert an equivalent amount of acetic anhydride to acetic acid as would be converted by the 5% methyl formate used in Examples 1 to 4. These comparison experiments were therefore equivalent.

5% by weight methyl formate was added to the autoclave charge in Examples 1 to 4. The effect on the ethylidene diacetate by-product formation was determined by stopping each reaction at a different reaction time.

The results of ethylidene diacetate formation during the comparison and in the Examples are shown in graph form in FIG. 1. This shows that the presence of methyl formate reduces the ethylidene di-acetate formation throughout the carbonylation reaction.

amount corresponding to 5% methyl formate to convert acetic anhydride to acetic acid. The results in Table 4 show that the addition of methyl formate in these experiments did not significantly change the amount of ethylidene diacetate by-product formed when the iodide salt used was N,N' dimethyl imidazolium iodide.

Further batch autoclave experiments were performed using a mixture of lithium iodide and N,N' dimethyl imidazolium iodide (QASI) as iodide salts. These are not examples according to the present invention because the iodide salt promoter, did not consist essentially of an alkali metal iodide salt and/or an alkaline earth metal iodide salt. The autoclave charges and the product analyses are given in

TABLE 1

AUTOCLAVE CHARGES

| Experiment/ Example | Methyl acetate (g) | Acetic anhydride (g) | Methyl iodide (g) | Acetic acid (g) | $[Rh(CO)_2Cl]_2$ (g) | Lithium iodide (g) | Methanol (g) | Methyl formate (g) | $H_2$ addition (barg) |
|---|---|---|---|---|---|---|---|---|---|
| A | 54.25 | 8.25 | 21.00 | 45.58 | 0.172 | 17.25 | — | — | 1.5 |
| B | 54.26 | 8.24 | 20.99 | 45.58 | 0.173 | 17.25 | — | — | 1.5 |
| C | 45.01 | 21.02 | 20.99 | 41.61 | 0.170 | 17.24 | 4.00 | — | 1.5 |
| D | 45.07 | 21.00 | 20.99 | 38.12 | 0.173 | 17.27 | 4.01 | — | 1.5 |
| 1 | 45.00 | 21.01 | 20.98 | 38.09 | 0.171 | 17.24 | — | 7.50 | 1.5 |
| 2 | 45.62 | 21.01 | 21.01 | 38.09 | 0.171 | 17.23 | — | 7.53 | 1.5 |
| 3 | 45.04 | 20.99 | 20.98 | 38.12 | 0.171 | 17.26 | — | 7.59 | 1.5 |
| 4 | 45.02 | 21.02 | 21.01 | 38.11 | 0.171 | 17.27 | — | 7.50 | 1.5 |

TABLE 2

PRODUCT ANALYSES.

| Experiment | Comment | Reaction Time (minutes) | Methyl acetate (% w/w) | Ethylidene diacetate (% w/w) | Acetone (% w/w) | $CO_2$ (% v/v) | $CH_4$ (% v/v) |
|---|---|---|---|---|---|---|---|
| A | Baseline | 19 | 18.7 | 0.046 | 0.067 | # | 0.3 |
| B | Baseline | 39 | 8.9 | 0.121 | 0.083 | 0.2 | 1.0 |
| C | Baseline (Methanol) | 70 | 2.8 | 0.276 | * | 0.5 | 2.1 |
| D | Baseline (Methanol) | 77 | 2.2 | 0.389 | 0.189 | 0.7 | 2.0 |
| 1 | 5% Methyl formate | 20 | 19.9 | 0.038 | * | 0.1 | 0.4 |
| 2 | 5% Methyl formate | 39 | 7.6 | 0.076 | 0.076 | 0.1 | 0.8 |
| 3 | 5% Methyl formate | 70 | 2.7 | 0.206 | 0.164 | 0.6 | 1.9 |
| 4 | 5% Methyl formate | 82 | 2.4 | 0.336 | 0.205 | 0.6 | 1.6 |

No $CO_2$ detected
*Peak not resolved

Further batch autoclave experiments were performed using N,N' dimethyl imidazolium iodide (QASI) as an iodide salt in place of lithium iodide. These are not examples according to the present invention as no alkali/alkaline earth metal iodide salt was used. The autoclave charges and the analyses of the products are given in Tables 3 and 4 respectively. Experiment F had methanol added in an Tables 5 and 6 respectively. Experiment J had formic acid added and Experiment K had methyl formate added. The results in Table 6 show that the addition of formic acid and methyl formate in these experiments did not significantly change the amount of ethylidene diacetate by-product formed when the iodide salt used was a mixture of N,N' dimethyl imidazolium iodide and lithium iodide.

TABLE 3

AUTOCLAVE CHARGES WITH N,N'DIMETHYL IMIDAZOLIUM IODIDE SALT (QASI).

| Experiment | Methyl acetate (g) | Acetic anhydride (g) | Methyl iodide (g) | Acetic acid (g) | $[Rh(CO)_2Cl]_2$ (g) | QASI (g) | Methanol (g) | Methyl formate (g) | $H_2$ addition (barg) |
|---|---|---|---|---|---|---|---|---|---|
| E | 45.02 | 21.02 | 21.02 | 33.96 | 0.171 | 28.89 | — | — | 1.5 |
| F | 45.03 | 21.00 | 21.00 | 26.50 | 0.173 | 28.84 | 4.04 | — | 1.5 |
| G | 45.02 | 21.02 | 21.03 | 26.49 | 0.171 | 28.87 | — | 7.56 | 1.5 |
| H | 45.06 | 21.04 | 21.00 | 27.18 | 0.172 | 28.88 | — | 7.52 | 1.5 |

TABLE 4

PRODUCT ANALYSES WITH N,N'DIMETHYL IMIDAZOLIUM IODIDE SALT.

| Experiment | Comment | Reaction Time (minutes) | Methyl acetate (% w/w) | Ethylidene diacetate (% w/w) | Acetone (% w/w) | $CO_2$ (% v/v) | $CH_4$ (% v/v) |
|---|---|---|---|---|---|---|---|
| E | Baseline | 69 | 2.8 | 0.512 | 0.214 | 1.0 | 1.7 |
| F | Methanol | 79 | 3.3 | 0.541 | 0.224 | 0.7 | 1.8 |
| G | 5% Methyl formate | 82 | 2.9 | 0.497 | 0.273 | 0.8 | 0.8 |
| H | 5% Methyl formate | 87 | 2.6 | 0.658 | 0.275 | 0.9 | 1.4 |

TABLE 5

AUTOCLAVE CHARGES WITH 1:1 MOLAR RATIO OF N,N'DIMETHYL IMIDAZOLIUM IODIDE (QASI) AND LITHIUM IODIDE AS IODIDE SALT PROMOTER.

| Experiment | Methyl acetate (g) | Acetic anhydride (g) | Methyl iodide (g) | Acetic acid (g) | $[Rh(CO)_2Cl]_2$ (g) | Lithium iodide (g) | QASI (g) | Addictive | $H_2$ addition (barg) |
|---|---|---|---|---|---|---|---|---|---|
| I | 45.00 | 21.02 | 21.02 | 39.86 | 0.170 | 8.63 | 14.42 | — | 1.5 |
| J | 45.00 | 21.02 | 20.98 | 38.30 | 0.171 | 8.65 | 14.42 | 1.50 formic acid | 1.5 |
| K | 45.01 | 21.02 | 21.02 | 38.57 | 0.172 | 8.63 | 14.46 | 1.50 Methyl formate | 1.5 |

TABLE 6

PRODUCT ANALYSES.

| Experiment | Comment | Reaction Time (minutes) | Methyl acetate (% w/w) | Ethylidene diacetate (% w/w) | Acetone (% w/w) | $CO_2$ (% v/v) | $CH_4$ (% v/v) |
|---|---|---|---|---|---|---|---|
| I | Baseline | 59 | 3.5 | 0.232 | 0.111 | 0.5 | 0.6 |
| J | 1% formic acid | 59 | 3.4 | 0.221 | 0.114 | 0.5 | 0.8 |
| K | 1% Methyl formate | 59 | 3.2 | 0.274 | 0.124 | 0.3 | 0.8 |

Batch autoclave experiments were also performed using formic acid in place of methyl formate, although in these experiments the reduction in ethylidene diacetate by-product formation was less than with methyl formate because of the more rapid breakdown of the formic acid. Autoclave charges and product analyses are shown in Tables 7 and 8 respectively.

TABLE 7

AUTOCLAVE CHARGES WITH FORMIC ACID ADDITION.

| Experiment | Methyl acetate (g) | Acetic anhydride (g) | Methyl iodide (g) | Acetic acid (g) | $[Rh(CO)_2Cl]_2$ (g) | LiI (g) | Formic acid (g) | $H_2$ addition (barg) |
|---|---|---|---|---|---|---|---|---|
| L | 45.00 | 21.00 | 21.00 | 45.60 | 0.170 | 17.24 | — | 1.5 |
| 5 | 44.99 | 21.01 | 20.99 | 36.94 | 0.171 | 17.24 | 7.50 | 1.5 |
| 6 | 45.01 | 20.99 | 21.01 | 38.10 | 0.171 | 17.24 | 7.54 | 1.5 |
| 7 | 45.02 | 21.00 | 21.00 | 41.66 | 0.170 | 17.24 | 2.99 | 1.5 |
| 8 | 45.01 | 17.64 | 20.99 | 44.12 | 0.170 | 17.24 | 1.52 | 1.5 |
| 9 | 45.01 | 21.02 | 20.99 | 44.08 | 0.171 | 17.23 | 1.49 | 1.5 |

TABLE 8

PRODUCT ANALYSES.

| Experiment | Comment | Reaction Time | Methyl acetate (% w/w) | Ethylidene diacetate (% w/w) | Acetone (% w/w) | $CO_2$ (% v/v) | $CH_4$ (% v/v) |
|---|---|---|---|---|---|---|---|
| L | Baseline | 64 | 2.7 | 0.264 | # | 0.5 | 2.0 |
| 5 | 5% formic acid | 62 | 3.6 | 0.126 | 0.112 | 0.3 | 0.7 |
| 6 | 5% formic acid | 61 | 2.2 | 0.249 | 0.080 | 0.3 | 1.5 |
| 7 | 2% formic acid | 60 | 2.6 | 0.256 | 0.156 | 0.4 | 1.2 |

TABLE 8-continued

PRODUCT ANALYSES.

| Experiment | Comment | Reaction Time | Methyl acetate (% w/w) | Ethylidene diacetate (% w/w) | Acetone (% w/w) | $CO_2$ (% v/v) | $CH_4$ (% v/v) |
|---|---|---|---|---|---|---|---|
| 8 | 1% formic acid | 62 | 2.9 | 0.223 | 0.176 | 0.4 | 1.5 |
| 9 | 1% formic acid | 65 | 2.7 | 0.247 | 0.174 | 0.4 | 1.2 | peak not resolved

In the batch autoclave experiments the rate of carbonylation was calculated at a calculated methyl acetate concentration of 20% by weight in the liquid reaction composition. This was calculated based upon the stoichiometry of the carbonylation reaction, assuming 100% selectivity and ideal gas laws and without any correction for volatile components in the autoclave headspace.

These results are shown in Table 9 below and show that the addition of methyl formate and/or formic acid did not have any adverse effect on the rate of carbonylation.

TABLE 9

CARBONYLATION RATES

| Exp./Example | Comment | Iodide salt promoter | Carbonylation rate (mol/l/hr)* |
|---|---|---|---|
| B | Baseline | lithium iodide | 6.7 |
| 3 | 5% methyl formate | lithium iodide | 7.8 |
| 6 | 5% formic acid | lithium iodide | 9.4 |
| 8 | 1% formic acid | lithium iodide | 8.2 |
| E | Baseline | N,N' dimethyl imidazolium iodide | 7.5 |
| G | 5% methyl formate | N,N' dimethyl imidazolium iodide | 7.6 |

*Rate at a calculated liquid reaction composition of 20% by weight methyl acetate.

Further Batch Autoclave Experiments

Batch autoclave experiments were performed to show the effect, of methyl formate addition to a carbonylation process using methyl-tri(n-butyl)phosphine iodide rather than lithium iodide as a source of iodide salt promoter. This phosphine iodide is used in comparative example 4 of Japanese laid-open patent application S62[1987]-145041.

The procedure used was similar to that for the previous batch autoclave experiments. The autoclave charges are set out in Table 10 below.

TABLE 10

| Charges (g) | Experiment M | Example N |
|---|---|---|
| methyl-tri(n-butyl)phosphine iodide | 14.6 | — |
| Lithium iodide | — | 5.68 |
| $Cr(CO)_6$ | 0.58 | 0.58 |
| $[Rh(CO)_2Cl]_2$ | 0.50 | 0.50 |
| Methyl acetate | 66.0 | 66.0 |
| Methyl formate | 64.0 | 64.0 |
| Methyl iodide | 24.0 | 24.0 |

The reagents were charged to the autoclave and after flushing with carbon monoxide 2940 kPaG (29.4 barg) carbon monoxide was added to the autoclave at room temperature. The autoclave was then heated to 170° C. and the autoclave was left at this temperature for 1 hour. The pressure was allowed to fall as carbon monoxide was consumed. At the end of this time, the autoclave was cooled, vented and the liquid reaction composition analysed as set out in table 11 below.

TABLE 11

| Component | Experiment M | Example N |
|---|---|---|
| methyl iodide (% by weight) | 16.2 | 16.2 |
| methyl acetate (% by weight) | 27.6 | 21.6 |
| acetic anhydride (% by weight) | 4.4 | 9.6 |

TABLE 11-continued

| Component | Experiment M | Example N |
|---|---|---|
| acetic acid (% by weight) | 31.0 | 33.9 |
| ethylidene diacetate (ppm) | 890 | 1040 |

These results show that with lithium iodide as the iodide salt promoter, considerably more acetic anhydride has been formed, and this has also led to more ethylidene diacetate being formed. Since in these batch experiments the liquid reaction composition in fact starts off without acetic anhydride being present due to the large amount of methyl formate charged to the autoclave, neither is an example according to the present invention as acetic anhydride is not maintained in the reaction composition. However, the use of lithium iodide causes sufficient acetic anhydride to be formed earlier in the reaction composition in Experiment N, that acetic anhydride is present earlier and hence longer during the experiment. This results in an increase in the amount of ethylidene diacetate being formed. It is expected that at comparable acetic anhydride production, the amount of ethylidene diacetate formed with the lithium iodide salt promoter would be less than with the phosphine iodide salt promoter.

Continuous Autoclave Experiments

Continuous autoclave experiments were performed in which liquid components and carbon monoxide gas were continuously introduced into an autoclave and liquid reaction composition continuously removed. This is a "once through" experiment in that there is no recycle of reaction composition components. Experiments were carried out in a 300 ml Hastelloy B2 autoclave reactor designed for continuous once-through operation. This unit was equipped with a Dispersimax™ agitator, carbon monoxide feed gas inlet, high pressure off-gas outlet, liquid feed inlet and reactor product outlet lines.

Mass balances of no less than 30 minutes were completed for each experiment. This period has been noted to be satisfactory under steady state conditions from previous experimental data.

An agitator speed of 1500 rpm, reactor temperature of either 189° C. or 199° C.±0.1° C. (controlled by a band heater), and a reactor level of 125 ml (by means of a level control loop) were employed for all experiments.

Precalculated liquid feed compositions, including concentrations of catalyst, lithium iodide promoter, and optionally formic acid or methyl formate, were charged to the reactor feed tank fitted with a balance. In line with predicted reaction rate and the required reactor composition for all components, liquid feed was pumped at a constant rate (typically 250 g/h) into the reactor. Feed gas (99.2% v/v carbon monoxide; 0.8% v/v hydrogen) was supplied from a cylinder, into the reactor on demand to maintain a constant set pressure. High pressure off-gas was also removed from the reactor head space to help maintain a constant carbon monoxide partial pressure by means of a flow control valve loop.

The amount of liquid reaction composition in the reactor was maintained by means of a control valve loop, the product removed from the reactor being collected in the product tank with fitted balance. The product composition was continuously analysed by Gas Chromatography so that any changes to the operation of the unit, which were necessary to reach or maintain the target reactor composition, could be recognised.

The carbonylation rate was determined by considering (i) rate based on methyl acetate consumed; and (ii) rate based on acetic acid and acetic anhydride produced. The mean of the two carbonylation rate calculations is reported within these examples and experiments.

Liquid feed and liquid product samples were analysed by Gas Chromatography for major components and liquid by-products Feed gas and off-gas were analysed for each experiment by Gas Chromatography to determine by-product gas make rates, in particular methane and water-gas-shift rates.

Experiment O

A baseline experiment was performed with a target composition of 18% w/w methyl acetate; 13.5% w/w acetic anhydride; 9% w/w methyl iodide; 6000 ppm Li; 620 ppm Rh at a reaction temperature of 199° C. The reaction was performed at a constant pressure of 3500 kPaG (35 barG) A steady carbonylation rate of 10.1 mol/l/hr rate was observed during the reaction, and subsequent analysis of the liquid by-products revealed a ethylidene diacetate level of 2720 ppm within the product acetic acid/acetic anhydride mixture.

This is not an example according to the present invention because no formic acid or methyl formate was introduced to the carbonylation reactor.

EXAMPLE 9

Experiment O was repeated except that formic acid (5% w/w) was added to the feed to the reactor. The rate of carbonylation was found to be 12.8 mol/l/hr and the ethylidene diacetate level was found to be 1020 ppm in the product acetic acid/acetic anhydride.

This is an example according to the present invention and it demonstrates that addition of formic acid reduces the level of ethylidene diacetate produced during the carbonylation.

EXAMPLE 10

Experiment O was repeated except that 5% w/w methyl formate was added to the feed to the reactor. The carbonylation rate was found to be 9.9 mol/l/hr whilst the ethylidene diacetate level was measured at 778 ppm in the product.

This example is according to the present invention and it demonstrates that addition of methyl formate reduces the amount of ethylidene diacetate produced.

Experiment P

A baseline experiment was performed with a target composition of 21% w/w methyl acetate; 2% w/w acetic anhydride 14% w/w methyl iodide; 7000 ppm Li; 700 ppm Rh at a reaction temperature of 189° C. The reaction was performed at a constant pressure of 3500 kPaG (35 barG). A steady carbonylation rate of 11.8 mol/l/hr rate was observed during the reaction, and subsequent analysis of the liquid by-products revealed a ethylidene diacetate level of 648 ppm in the product acetic acid/acetic anhydride mixture.

This is not an example according to the present invention because no formic acid or methyl formate was introduced to the carbonylation reactor.

EXAMPLE 11

Experiment P was repeated except that 5% w/w formic acid was also charged to the reaction feed tank. The carbonylation rate was found to be 12.9 mol/l/hr whilst the level of ethylidene diacetate in the product acetic acid/acetic anhydride was 413 ppm.

This example is according to the present invention and it demonstrates that at lower acetic anhydride concentrations in the liquid reaction composition, the production of the ethylidene diacetate by-product is still reduced on addition of formic acid.

The results of the above experiments and examples are summarised in Table 12 below.

TABLE 12

|  | Acetic anhydride (% w/w) | Carbonylation rate (mol/l/hr) | Methane make (% of carbonylation rate) | Carbon dioxide make (% of carbonylation rate) | Ethylidene diacetate (ppm) |
| --- | --- | --- | --- | --- | --- |
| Experiment O | 11.9 | 10.1 | 0.07 | 0.11 | 2720 |
| Example 9 | 13.4 | 12.8 | 0.05 | 0.07 | 1020 |
| Example 10 | 13.6 | 9.9 | 0.02 | 0.04 | 778 |

TABLE 12-continued

|  | Acetic anhydride (% w/w) | Carbonylation rate (mol/l/hr) | Methane make (% of carbonylation rate) | Carbon dioxide make (% of carbonylation rate) | Ethylidene diacetate (ppm) |
|---|---|---|---|---|---|
| Experiment P | 4.1 | 11.8 | 0.02 | 0.04 | 648 |
| Example 11 | 3.1 | 12.9 | 0.02 | 0.03 | 413 |

Further Batch Autoclave Experiments

EXPERIMENT Q AND EXAMPLE 12

In the following experiments, calcium iodide was used as the iodide salt promoter. The apparatus and procedure was the same as described hereinbefore under Batch Autoclave Experiments—General Experimental procedure.

The autoclave charges are shown in Table 13 and the rate/yield data in Table 14.

TABLE 13

Autoclave chargers Experiment Q and Example 12.

|  | Methyl acetate (g) | Acetic anhydride (g) | Methyl iodide (g) | Acetic acid (g) | [Rh(CO)$_2$Cl]$_2$ (g) | CaI$_2$ (g) | Methyl formate (g) | H$_2$ addition (barg) |
|---|---|---|---|---|---|---|---|---|
| Experiment Q | 54.28 | 8.25 | 21.00 | 43.94 | 0.169 | 18.93 | — | 1.5 |
| Example 12 | 45.00 | 21.00 | 21.01 | 36.43 | 0.170 | 18.92 | 7.51 | 1.5 |

TABLE 14

Experiment Q and Example 12.

|  | Additive | I$^-$ Source | Run Time (mins) | End Methyl acetate (% w/w) | EDAc (% w/w) | CO$_2$ (% v/v) | CH$_4$ (% v/v) |
|---|---|---|---|---|---|---|---|
| Experiment Q | CaI$_2$ Baseline | CaI$_2$ | 70 | 8.7 | 0.172 | 0.1 | 1.1 |
| Example 12 | CaI$_2$/Methyl formate | CaI$_2$ | 70 | 11.2 | 0.103 | 0.2 | 0.9 |

In these two experiments CaI$_2$ was used as the ionic iodide source in the carbonylation. A baseline (Experiment Q) was carried out as well as an experiment (Example 12) where 5% methyl formate was added. In each case the experiment was run for 70 minutes. The results show that addition of methyl formate leads to a significant reduction in the amount EDAc formed in the reaction (40% reduction). Thus, as with experiments where lithium iodide is used as the sole source of ionic iodide, methyl formate is seen to reduce the formation of EDAc.

EXPERIMENTS R AND EXAMPLE 13

Comparison of Lithium Iodide and Methyl-tri(n-butyl)phosphine Iodide as Iodide Source In the following experiments, lithium iodide and methyl-tri(n-butyl)phosphine iodide were compared as the iodide salt promoter. Therefore Experiment R is not according to the present invention but Example 13 is according to the present invention.

The apparatus and procedure was the same as described hereinbefore under Batch Autoclave Experiments—General Experimental procedure.

The autoclave charges are shown in Table 15 and the rate/yield data in Table 16.

Whilst the use of this phosphine iodide in Experiment R gives similar levels of EDAc in the presence of methyl formate compared to lithium iodide in Example 13, the rate of reaction with the phosphine iodide is considerably slower (it takes 44% longer to reach a comparable conversion).

TABLE 15

Experiment R and Example 13 - Autoclave charges

| Experiment | Methyl acetate (g) | Acetic anhydride (g) | Methyl iodide (g) | Acetic acid (g) | [Rh(CO)$_2$Cl]$_2$ (g) | Iodide Source (g) | Methyl formate (g) | H$_2$ addition (barg) |
|---|---|---|---|---|---|---|---|---|
| 13 | 45.04 | 20.99 | 20.98 | 38.12 | 0.171 | 17.26 | 7.59 | 1.5 |
| R | 45.00 | 21.00 | 21.02 | 11.07 | 0.173 | 44.32 | 7.50 | 1.5 |

TABLE 16

Experiment R and Example 13.

| Experiment | Additive | I⁻ Source | Run Time (mins) | End Methyl acetate (% w/w) | EDAc (% w/w) | $CO_2$ (% v/v) | $CH_4$ (% v/v) |
|---|---|---|---|---|---|---|---|
| 13 | 5% Me formate | LiI | 70 | 2.7 | 0.206 | 0.6 | 1.9 |
| R | 5% Me formate | Me($^n$Bu)$_3$PI | 101 | 3.2 | 0.210 | 0.9 | 0.5 |

We claim:

1. A process for the co-production of acetic anhydride and acetic acid which process comprises introducing a carbonylatable feedstock comprising methyl acetate and/or dimethyl ether and optionally also comprising methanol and/or water, to a carbonylation reactor in which there is maintained a liquid reaction composition comprising acetic anhydride, acetic acid, rhodium carbonylation catalyst, alkyl iodide co-catalyst and an iodide salt promoter consisting essentially of an alkali metal iodide and/or alkaline earth metal iodide, contacting said carbonylatable feedstock with carbon monoxide in said liquid reaction composition to produce acetic anhydride and acetic acid, and introducing to the carbonylation reactor methyl formate and/or formic acid in the range from 0.1 to 20% by weight of the total feed of liquid components to the reactor.

2. A process as claimed in claim 1 in which the amount of methyl formate and/or formic acid is in the range 0.1 to 10% by weight of the total feed of liquid components to the reactor.

3. A process as claimed in claim 1 in which methyl formate is present in the liquid reaction composition at a concentration of greater than zero to 1000 ppm.

4. A process as claimed in claim 1 in which formic acid is present in the liquid reaction composition at a concentration of greater than zero to 100 ppm.

5. A process as claimed in claim 2 in which methyl formate is present in the liquid reaction composition at a concentration of greater than zero to 1000 ppm.

6. A process as claimed in claim 2 in which formic acid is present in the liquid reaction composition at a concentration of greater than zero to 100 ppm.

7. A process as claimed in claim 1 in which the concentration of the iodide salt promoter in the liquid reaction composition is in the range from 1 to 40% by weight.

8. A process as claimed in claim 1 in which the iodide salt consists essentially of lithium iodide and/or calcium iodide.

9. A process as claimed in claim 1 in which the carbonylatable feedstock is selected from the group consisting of methyl acetate/methanol mixtures, dimethyl ether/methanol mixtures and methyl acetate/methanol/water mixtures.

10. A process as claimed in claim 1 in which the acetic acid and acetic anhydride product are recovered from the carbonylation reactor, by continuously removing a portion of the liquid reaction composition from the carbonylation reactor, recovering the acetic acid and acetic anhydride products therefore and recycling the remaining components to the carbonation reactor.

* * * * *